(12) United States Patent
Ihlenfeldt et al.

(10) Patent No.: US 7,625,735 B2
(45) Date of Patent: Dec. 1, 2009

(54) RECOMBINANT KINASE FROM INSECT CELLS FOR THE SYNTHESIS OF NUCLEOSIDE MONOPHOSPHATES

(75) Inventors: Hans-Georg Ihlenfeldt, Iffeldorf (DE); Brigitte Munch-Petersen, Farum (DK); Jure Piskur, Copenhagen (DK); Leif Sondergaard, Gentofte (DK)

(73) Assignee: Roche Diagnostic Operations, Inc., Indianapolis, IN (US)

( * ) Notice: Subject to any disclaimer, the term of this patent is extended or adjusted under 35 U.S.C. 154(b) by 326 days.

(21) Appl. No.: 10/680,635

(22) Filed: Oct. 7, 2003

(65) Prior Publication Data

US 2006/0252131 A1 Nov. 9, 2006

Related U.S. Application Data

(63) Continuation of application No. 09/416,579, filed on Oct. 12, 1999, now abandoned.

(30) Foreign Application Priority Data

Oct. 12, 1998 (DE) ................................ 198 46 838
Mar. 31, 1999 (DE) ................................ 199 14 644

(51) Int. Cl.
*C12N 9/12* (2006.01)
*C07H 21/02* (2006.01)

(52) U.S. Cl. ...................................... 435/194; 536/23.1

(58) Field of Classification Search ....................... None
See application file for complete search history.

(56) References Cited

OTHER PUBLICATIONS

Munch-Petersen et al. (Feb. 13, 1998) The Journal of biological Chemistry, vol. 273, p. 3926-3931.*
Johansson et al. (Aug. 20, 1999) The Journal of biological Chemistry, vol. 274, p. 23814-23819.*
Eriksson, S., Wang, L., "Substrate Specificities, Expression and Primary Sequences of Deoxynucleoside Kinases; Implications for Chemotherapy", Nucleosides & Nucleotides, 16(5&6), 653-659 (1997).
Sherley, J.L., Kelly, T.J., "Human Cytosolic Thymidine Kinase", The Journal of Biological Chemistry, vol. 263, No. 1, Jan. 5, 1988, pp. 375-382.
Bohman, C., Eriksson, S., "Deoxycytidine Kinase from Human Leukemic Spleen: Preparation and Characterization of the Homogeneous Enzyme", Biochemistry, 1988, 27, 4258-4265.
Cheng, Y.C., Ostrander, M., "Deoxythymidine Kinase Induced in HeLa TK-Cells by Herpes Simplex Virus Type I and Type II", The Journal of Biological Chemistry, vol. 251, No. 9, May 10, 1976, pp. 2605-2610.
Ellims, P.H., Gan, T.E., Cosgrove, L. "Human thymidine kinase: purification and some properties of the TK1 isoenzyme from placenta", Molecular and Cellular Biochemistry 45, 113-116 (1982).
Gan, T.E., Brumley, J.L., Van Der Weyden, M.B., "Human Thymidine Kinase", The Journal of Biological Chemistry, vol. 258, No. 11, Jun. 10, 1983, pp. 7000-7004.
Bjarne Hove-Jensen, et al., A meeting on "Enzyme Families in Nucleotide Metabolism", Krogerup Conference Centre Humlebaek, DK-3050, Aug. 23-28, 1997, Center for Enzyme Research, Institute of Molecular Biology University of Copenhagen.
Kierdaszuk, B., Eriksson, S. "Selective Inactivation of the Deoxyadenosine Phosphorylating Activity of Pure Human Deoxycytidine Kinase: Stabilization of Different Forrns of the Enzyme by Substrates and Biological Detergents." Biochemistry, 1990, 29., pp. 4109-4114.
Lee, L.S., Cheng, Y.C., "Human Deoxythymidine Kinase", The Journal of Biological Chemistry, vol. 251, No. 9, May 10, 1976, pp. 2600-2604.
Munch-Petersen, B., Cloos, L., Tyrsted, G., Eriksson, S. "Diverging Substrate Specificity of Pure Human Thymidine Kinases 1 and 2 Against Antiviral Dideoxynucleosides", The Journal of Biological Chemistry, vol. 266, No. 14, May 15, 1991, pp. 9032-9038.
Munch-Petersen, B., "DNA Precursor Pool Balance and Thymidine Kinase Isoenzymes in Normal and Malignant Cells. Enzymatic Regulation Mechanisms and Clinical Therapeutic Applications", Institute of Life Sciences and Chemistry, Roskilde University, Denmark, 1996, pp. 1-166.
Munch-Petersen, B., Piskur, J., Sondergaard, L. "Four Deoxynucleoside Kinase Activities from Drosophila melanogaster Are Contained within a Single Monomeric Enzyme, a New Multifunctional Deoxynucleoside Kinase." The Journal of Biological Chemistry, vol. 273, No. 7, Feb. 13, 1998, pp. 3926-2931.

* cited by examiner

*Primary Examiner*—David J Steadman
*Assistant Examiner*—Alexander D Kim
(74) *Attorney, Agent, or Firm*—Barnes & Thornburg LLP (57) ABSTRACT

A recombinant *Drosophila melanogaster* deoxynucleoside kinase that remains stable during the synthesis of nucleoside monophosphate without the addition of stabilizing SH reagents or stabilizing proteins, and that accepts all four natural deoxynucleotides is provided. In addition, the invention concerns DNA sequences, vectors, transformed cells, a method for production of the recombinant kinase as well as its use for preparing nucleoside monophosphates.

5 Claims, 8 Drawing Sheets

Figure 1    Kinetic constants of deoxynucleoside kinases

|  |  | dThd | dCyd | dAdo | dGuo | ATP |
|---|---|---|---|---|---|---|
| Dm-dNK | $k_c$ (1/s) | 15 | 15 | 17,8 | 18,9 | 15 |
|  | $K_m$ (μM) | 0,9 | 1 | 109 | 650 | 1 |
|  | $k_c/K_m$ $M^{-1}s^{-1}$ | $1,7 \times 10^7$ | $1,5 \times 10^7$ | $1,6 \times 10^5$ | $2,9 \times 10^4$ | $1,5 \times 10^7$ |
| hTK1 (a) | $k_c$ (1/s) | 4,2 |  |  |  | 4,2 |
|  | $K_m$ (μM) | 0,5 |  |  |  | 140 |
|  | $k_c/K_m$ $M^{-1}s^{-1}$ | $8,3 \times 10^6$ |  |  |  | $3 \times \times 10^4$ |
| hTK2 (b) | $k_c$ (1/s) | 0,3 | 0,4 |  |  | ,0,3 |
|  | $K_m$ (μM) | 16 | 16 |  |  | 2 |
|  | $k_c/K_m$ $M^{-1}s^{-1}$ | $1,9 \times 10^4$ | $2,5 \times 10^4$ |  |  | $1,5 \times 10^5$ |
| hdCK (c) | $k_c$ (1/s) |  | 0,073 | 0,31 | 0,4 | 0,073 |
|  | $K_m$ (μM) |  | 1 | 120 | 150 | 10 |
|  | $k_c/K_m$ $M^{-1}s^{-1}$ |  | $7,3 \times 10^4$ | $2,6 \times 10^3$ | $2,7 \times 10^3$ | $7,3 \times 10^3$ |
| hdGK (d) | $k_c$ (1/s) |  |  | $1,35 \times 10^{-3}$ | $2,1 \times 10^{-3}$ |  |
|  | $K_m$ (μM) |  |  | 60 | 7,6 |  |
|  | $k_c/K_m$ $M^{-1}s^{-1}$ |  |  | $2,3 \times 10^1$ | $2,8 \times 10^2$ |  |
| E. Coli TK (e) | $k_c$ (1/s) | 1,6 |  |  |  | 1,6 |
|  | $K_m$ (μM) | 9 |  |  |  | 500 |
|  | $k_c/K_m$ $M^{-1}s^{-1}$ | $1,8 \times 10^5$ |  |  |  | $3,2 \times 10^3$ |
| HSV TK (f) | $k_c$ (1/s) | 0,21 |  |  |  | 0,21 |
|  | $K_m$ (μM) | 0,6 |  |  |  | 32 |
|  | $k_c/K_m$ $M^{-1}s^{-1}$ | $3,8 \times 10^5$ |  |  |  | $6,6 \times 10^3$ |
| Lactobac. dAK/dCK (g) or dGK | $k_c$ (1/s) |  | 0,91 | 0,05 | 0,7 | 0,91 |
|  | $K_m$ (μM) |  | 4,5 | 8,4 | 7,8 | 1000 |
|  | $k_c/K_m$ $M^{-1}s^{-1}$ |  | $2 \times 10^5$ | $6 \times 10^3$ | $8,9 \times 10^4$ | $9,1 \times 10^2$ |

Seq. ID No.: 1

```
            ATG GCG GAG GCA GCA TCC TGT GCC CGA AAG GGG ACC AAG TAC GCC
GAG GGC ACC CAG CCC TTC ACC GTC CTC ATC GAG GGC AAC ATC GGC AGC GGG
AAG ACC ACG TAT TTG AAC CAC TTC GAG AAG TAC AAG AAC GAC ATT TGC CTG
CTG ACC GAG CCC GTC GAG AAG TGG CGC AAC GTC AAC GGG GTA AAT CTG CTG
GAG CTG ATG TAC AAA GAT CCC AAG AAG TGG GCC ATG CCC TTT CAG AGT TAT
GTC ACG CTG ACC ATG CTG CAG TCG CAC ACC GCC CCA ACC AAC AAG AAG CTA
AAA ATA ATG GAG CGC TCC ATT TTT AGC GCT CGC TAT TGC TTC GTG GAG AAC
ATG CGA CGA AAC GGC TCG CTG GAG CAG GGC ATG TAC AAT ACG CTG GAG GAG
TGG TAC AAG TTC ATC GAA GAG TCC ATT CAC CTG CAG GCG GAC CTC ATA ATA
TAT CTG CGC ACC TCG CCG GAG GTG GCG TAC GAA CGC ATC CGG CAG CGG GCT
CGT TCT GAG GAG AGC TGC GTG CCG CTT AAG TAC CTT CAG GAG CTG CAT GAG
TTG CAC CAG GAC TGG TTG ATA CAC CAG AGA CGA CCG CAG TCG TGC AAG GTC
CTA GTC CTC GAT GCC GAT CTG AAC CTG GAA AAC ATT GGC ACC GAG TAC CAG
CGC TCG GAG AGC AGC ATA TTC GAC GCC ATC TCA AGT AAC CAA CAG CCC TCG
CCG GTT CGT GTG TCG CCC AGC AAG CGC CAG AGG GTC GCC AGA TAA
```

RECOMBINANT KINASE FROM INSECT CELLS FOR THE SYNTHESIS OF NUCLEOSIDE MONOPHOSPHATES

This application is a continuation of U.S. Ser. No. 09/416,579 filed Oct. 12, 1999, now abandoned, which claims priority to German application LYE. 19914644.6 filed Mar. 31, 1999, and to German application DE 19846838.5 filed Oct. 12, 1998.

The subject of the present invention is a recombinant kinase from insect cells such as e.g. *Drosophila Melanogaster*, remaining stable during the synthesis of nucleoside monophosphates without the addition of stabilizing SH reagents, without stabilizing proteins and detergents and accepting all four natural deoxynucleosides. A further subject matter of the present invention is a DNA sequence encoding the kinase according to the invention as well as a procedure for preparation of the kinase according to the invention and its use during the synthesis of nucleoside monophosphates.

(Deoxy)-nucleoside kinases catalyze the phosphorylation of nucleosides or deoxynucleosides, respectively, to the corresponding nucleotide monophosphates and have therefore an important role in the "salvage pathway" of the nucleotide metabolism.

The catalyzed reaction is:

The deoxynucleoside monophosphates are starting products for the deoxynucleoside tri-phosphates which are used to a very increasing extent as reagents for the PCR reaction.

The deoxynucleoside monophosphates are at present accessible by three ways:

1. from hydrolysis of fish sperm
2. by chemical synthesis from deoxynucleosides
3. by enzymatic synthesis from deoxynucleosides.

The hitherto known methods have a number of disadvantages. Thus, during the hydrolysis of fish sperm all 4 monophosphates are produced in about the same quantities; this is a fact that misses the requirements of the market (e.g. d-UTP, partially used instead of d-TTP is prepared from d-CTP). In addition, d-TTP, resulting from hydrolysis, is contaminated with approx. 2% d-UTP and can, practically, not be isolated.

Furthermore, the animal origin of the educts has to be assessed as critical from a regulatory point of view (GMP). Moreover, the market of monophosphates from fish sperm is very limited.

A number of side products are produced during the chemical synthesis which are difficult to separate by chromatographic purification. In addition, several bases (e.g. guanosine) must be provided with protective groups before phosphorylation which increases the synthesis time considerably.

The disadvantages of the state of the art were overcome by the provision of a recombinant multifunctional deoxynucleoside kinase from insect cells such as, in particular, *Drosophila Melanogaster* (Dm-dNK) remaining stable during the synthesis of nucleoside monophosphates without the addition of stabilizing SH reagents, without stabilizing proteins and detergents and accepting all four natural deoxynucleosides: thymidine (dThd), deoxycytidine (dCyd), deoxyadenosine (dAdo) and deoxyguanosine (dGuo). In the present invention stable means that the yield rate for the catalyzed reaction does practically not decrease within 5 hours, preferably 10 hours, particularly preferably within 12 hours at 37° C. It is surprising that the enzyme remains stable for such a long time without addition of stabilizers containing thiol. This stability has not been observed in other kinases until now (1-9). By leaving out these stabilizers when using the kinase according to the invention in the synthesis the synthesis gets cheaper and, above all, the product purification can be simplified to a great extent.

Figure 1:
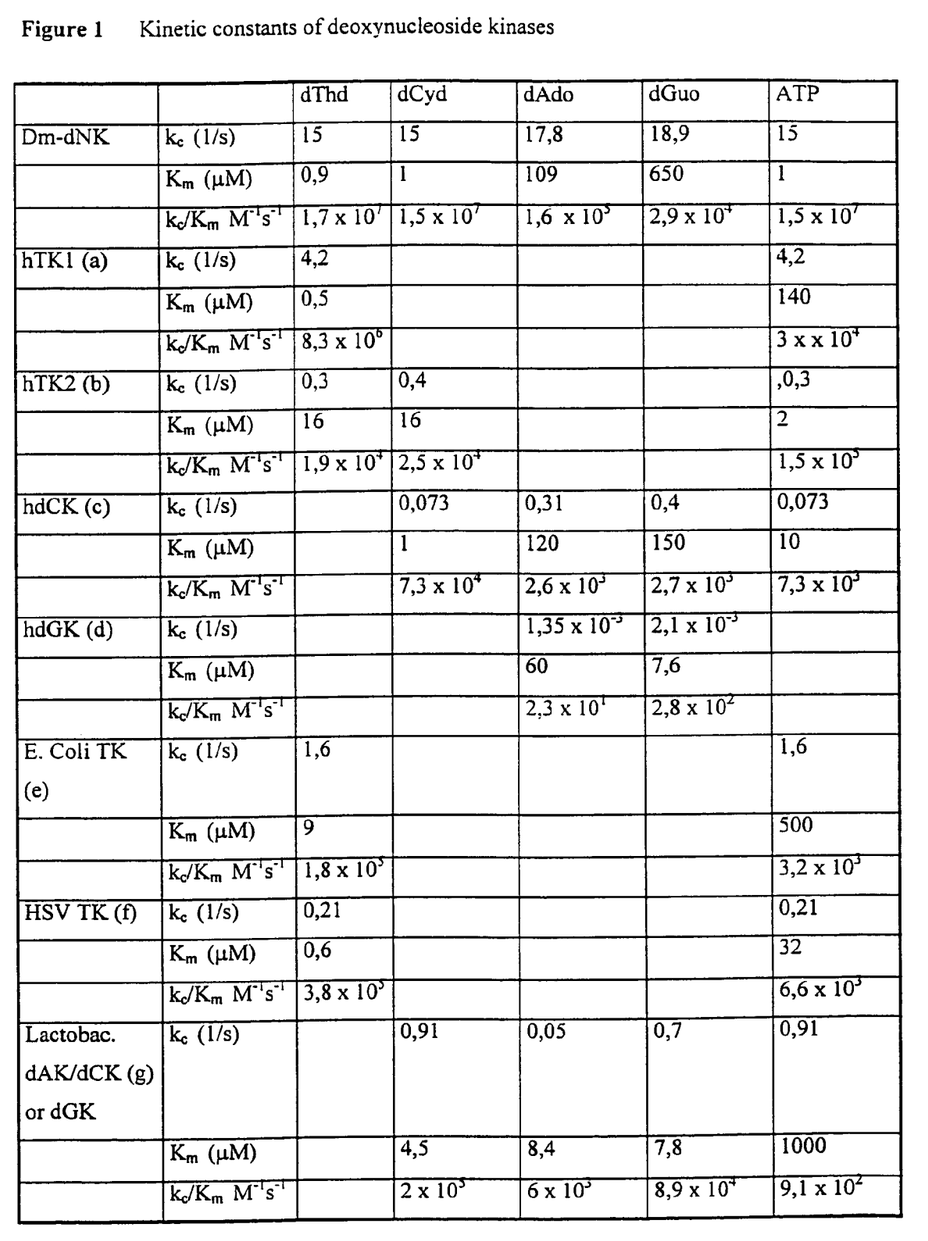

Furthermore, hitherto known kinases have a considerably higher substrate specificity; as a consequence, for the synthesis of the individual nucleosides it is no more necessary to have the corresponding specific kinase. Particularly advantageous is the low specificity for the synthesis of modified nucleoside analogues, such as dideoxynucleosides or base- or sugar-modified nucleosides. Base-modified nucleosides are for example 7-deaza-nucleosides, C-nucleosides and nucleotides labelled with reporter groups (dye, digoxigenin, biotin) at the base. Sugar-modified nucleosides are for example azathymidine, arabinosyl-thymidine. The kinetic constants of the *Drosophila* kinase compared to known analogous enzymes are listed in table 1. The specific activity kc of the kinase according to the invention is several times higher than that of the kinases known before. The activity of the enzyme was measured as described in the reference: Munch-Peterson et al. (1991) J. Biol. Chem. 266, 9032-9038. By this, a considerably lower amount of enzyme is necessary to synthesize the dNMPs. (factor 3.5-14000, cf. Kc values in table 1). The specificity constant ($k_c/K_M$) of the kinase according to the invention exceeds that of the hitherto known kinases by several powers and is in the region of the diffusion constant. This leads to the complete yield when the kinase is added to the d-NMP synthesis. They are higher by factor 2-6500 than the hitherto known kinases, s. FIG. 1.

Surprisingly, the enzyme according to the invention is still stable at 60° C. what is advantageous for the reaction procedure. Preferably, the enzyme according to the invention has at T=37° C. a half-life of $t_{1/2} \geq 50$ h in Tris buffer with 5 mM $MgCl_2$ and $t_{1/2} \geq 25$ h in water and accepts all natural deoxynucleosides (example 6).

A further subject matter of the invention are kinases from other non-vertebrate organisms, in particular from other animal species of the Hexapoda class showing comparable properties to those of the *Drosophila* kinase. Particularly such kinases essentially having the above described stability and the above described substrate specificity. Peferred kinases are those isolated from the subclass of Pterygota and particularly preferable are those from the Diptera class, particularly preferable from the Drosophilidae family.

A further subject matter of the invention is a DNA sequence as well as functional fragments thereof coding for the kinase according to the invention. The DNA sequence according to the invention is characterized in that the primers listed in the following hybridize onto the DNA sequence of the kinase according to the invention:

```
                                           SEQ ID No.: 2
GGGAAGTGGCAGGAGTAGCTCCCG

SEQ ID No.: 3
CTCCCGTTGTAGCCGTCGCCCTTCTGG

SEQ ID No.: 4
GACGACTGGCTCGGGCAGCTCTTCACCGCGTTG

SEQ ID No.: 5
TTCGATTTTTATTACCTCGCGAGGTAA

SEQ ID No.: 6
AGGTAAAAATCGCGAGCGATAACGAAGCAC

SEQ ID No.: 7
CACCGCATGCTTGCGTAGGCCGTCGCCCGAGCAAGACTCCTC

SEQ ID No.: 8
GACTACATGTTTCTAGGGTTCTTCACC
```

A further subject matter of the invention are also such kinases and DNA sequences onto the DNA sequence of which hybridize oligonucleotides with the SEQ ID No.: 2, 3, 5, 7 and 8 or with the SEQ ID No.: 2, 4, 5, 7 and 8 or with the SEQ ID No.: 5, 6, 7 and 8.

The following hybridization conditions are advantageous:

Hybridization: 0.75 m NaCl, 0.15 Tris, 10 mM EDTA. 0.1% sodium pyrophosphate, 0.1% SLS, 0.03% BSA, 0.03% Ficoll 400, 0.03% PVP and 100 μd/ml boiled calf thymus DNA at 50° C. for approx. 12 hours.

Washing: 3×30 minutes with 0.1×SET, 0.1% SDS, 0.1% sodium pyrophosphate and 0.1 M phosphate buffer at 45° C.

Figure 5:
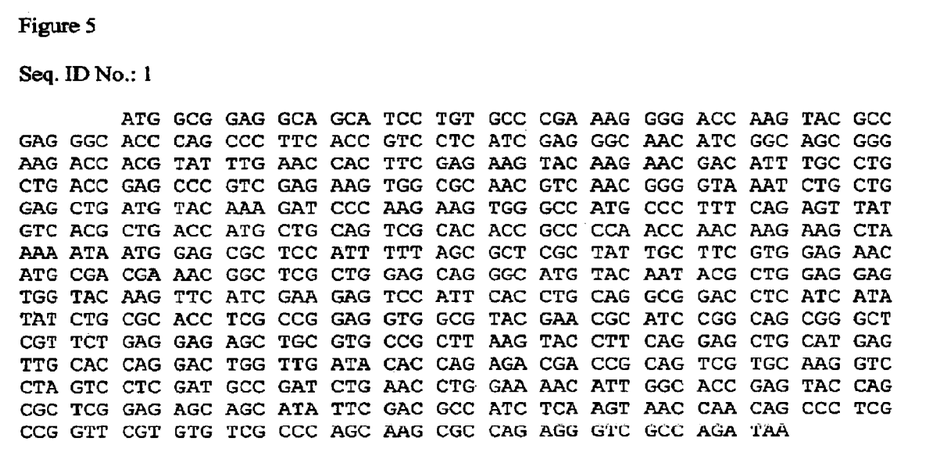
FIG. 5 shows the DNA sequence of the clone.

The kinase sequence according to the invention is given in FIG. 5, SEQ ID No.: 1.

The DNA sequence according to the invention is obtainable from *Drosophila Melanogaster* by the procedure described in the following:

A pBluescript SK+/− phagmide containing a 1.1 kbp cDNA insert which contains among others the presumed gene coding for the deoxynucleoside kinase was obtained from the Berkeley *Drosophila* genome sequencing project (clone LD15983). The first 600 base pairs of the 5' end of the 1.1 kbp cDNA cloned via EcoRI and XhoI in the multiple cloning site (MCS) of the phagmide were already sequenced by Harvey et al., University of Calif., Berkeley. Based on these sequence information new primers were designed (Dm-TK1 and Dm-TK2/SEQ ID NO.9: 5'TCCCAATCTCACGTGCA-GATC-3' and SEQ ID NO 10: 5'-TTCATCGAAGAGTC-CATTCAC-3' which enabled complete sequencing of the insert. Dm-TK1 is a 21 bp sense primer binding upstream from the presumed translation start region. Dm-TK2 was designed as 21 bp sense primer according to the 3' region of the cDNA part already sequenced.

With this sequence an open reading frame including 750 bp and coding for a protein with 250 amino acids could be identified. The DNA sequence SEQ ID NO.1 is depicted in FIG. 5. The calculated molecular weight of this protein was 29 kDa and corresponds therefore to the data given by Munch-Peterson et al. 1998 indicating a weight of nearly 30 kDa for native Dm-dNK.

Starting from the sequence information the structure gene coding for the Dm-dNK could be isolated from the 1.1 kbp cDNA insert of the pBluescript SK+/− phagmide by the "polymerase chain reaction" technique (PCR) (Mullis, K. B. and Faloona F. A., Methods in Enzymol. 155 (1987) 335-350). For this, a specific primer pair (see SEQ ID NO.11: 5'-GCGCGAATTCATGGCGGAGGCAGCATCCTGTGC-3' and SEQ ID NO. 12: 5'-GCGCAAGCTTATTATCTGGC-GACCCTCTGGC-3') with the corresponding endonuclease restriction site of the later insertion into appropriate expression plasmids was synthesized. Thus, the 5'-primer (Dm-dNK3) has an EcoRI endonuclease restriction site upstream from the coding sequence whereas the 3'-primer (Dm-dNK4) contains a HindIII endonuclease restriction site downstream from the coding sequence. Furthermore, the 3'-primer contains downstream from to the coding sequence two stopcodons for safe termination of the translation. Further, suitable primers which were optimized for the translation initiation in *E. coli* were the following:

```
(Dm-dNK 3)
                                          SEQ ID No.: 13
5'-CGCGAATTCA TGGCGGAAGC GGCGAGCTGC GCGCGTAAGG
GGACC-3'

(Dm-dNK 4)
                                          SEQ ID No.: 14
5'-CGCAAGCTTA TTAACGGGCG ACCCTCTGGC-3'
```

Cloning of the Structure Gene for the Dm-dNK in pUC18

The PCR preparation was applied to an agarose gel and the 750 Bp structure gene was isolated from the agarose gel. The PCR fragment was cut with the EcoRI and HindIII restriction endonucleases for 1 hour at 37° C. Simultaneously, the pUC18 plasmid was cut with the EcoRI and HindIII restriction endonucleases for 1 hour at 37° C., the preparation was then separated by agarose gel electrophoresis and the 2635 Bp vector fragment isolated. Subsequently, the PCR fragment and the vector fragment were ligated by T4-DNA-ligase. Then 1 μl (20 ng) of vector fragment and 3 μl (100 ng) of PCR fragment, 1 μl 10× ligase buffer (Maniatis et al., 1989 Molecular cloning, a laboratory manual, Sambrok, Fritsch, Maniatis, Book 3, Section B27; Munch-Peterson (1991) J. Biol. Chem. 266, 9032), 1 μl T4-DNA-ligase. 4 μl sterile H₂O bidist were pipetted, carefully mixed and incubated over night at 16° C.

The cloned gene was checked by means of restriction analysis and by sequencing.

Cloning of the Structure Gene for the Dm-dNK in Appropriate Expression Vectors

For expression of the Dm-dNK the structure gene was cloned in appropriate expression vectors in such a way that the structure gene is inserted in the right orientation under the control of an appropriate promoter, preferably an inducible promoter, particularly preferably the lac-, lacUV5-, tac- or T5 promoter. Preferred expression vectors are pUC plasmids with lac- or lacUV5 promoters or pKK plasmids.

For this, the structure gene was cut out of the plasmid pUC18 for the Dm-dNK by means of EcoRI and HindIII, the restriction preparation was separated by agarose gel electrophoresis and the approx. 750 Bp fragment was isolated from the agarose gel. Simultaneously, the expression vectors were cut with EcoRI and HindIII, the restriction preparation was separated by agarose gel electrophoresis and the resulting vector fragment was isolated from the agarose gel. The resulting fragments were ligated as described. The appropriate insertion of the gene was verified by restriction analysis and sequencing.

Preferred expression vectors are also pUC18, pKK177-3, pKKT5. Especially preferred is pKKT5. The expression vector pKKT5 is obtained from pKK177-3 (Kopetzki et al. 1989, Mol. Gen. Genet. 216:149-155) by exchanging the tac- promotors with the T5-promoter derived from the plasmid pDS (Bujard et al. 1987, Methods Enzymol. 155:416-433). The EcoRI-endonuclease restriction site was removed from the sequence of the T5-promotor by point mutation.

Transformation of the Expression Vectors in Different *E. coli* Expression Strains Competent cells of different *E. coli* strains were prepared according to the Hanahan method (J. Mol. Biol. 166 (1983) pp. 557). 200 µl of the resulting cells were mixed with 20 ng of isolated plasmid DNA (expression vectors). After 30 min. incubation on ice a thermal shock (90 sec. at 42° C.) was carried out. Subsequently, the cells were transferred in 1 ml LB-medium and incubated for phenotypical expression for 1 hour at 37° C. Aliquots of this transformation preparation were plated on LB plates with ampicillin as a selection marker and then incubated for 15 hours at 37° C.

Appropriate host cells are *E. coli* K12 JM83, JM101, JM105, NM522, UT5600, TG1, RRIΔM15, *E. coli* HB101, *E. coli* B.

Expression of Dm-dNK in *E. coli*

For the expression of Dm-dNK clones containing plasmid were inoculated in 3 ml Lb$_{amp}$ medium and incubated in the shaker at 37° C. At an optical density of 0.5 at 550 nm the cells were induced with 1 mM IPTG and incubated in the shaker for 4 hours at 37° C. Subsequently, the optical density of the individual expression clones was determined, an aliquot with an OD$_{550}$ of 3/ml was taken and the cells were centrifuged (10 min. at 6000 rpm, 4° C.). The cells were re-suspended in 400 µl TE buffer (50 mM TRIS/50 mM EDTA, pH 8.0), released by ultrasound and then the soluble protein fraction was separated from the insoluble protein fraction by centrifugation (10 min., 14000 rpm, 4° C.). A buffer containing SDS and β-mercaptoethanol was added to all fractions and the proteins were denatured by boiling (5 min. at 100° C.). Subsequently, each quantity of 10 µl was analyzed by means of a 15% analytical SDS gel (Laemmli U.K. (1970) *Nature* 227: pp. 555-557).

A further subject matter of the invention is a method for production of the nucleoside monophosphates which is characterized in more detail by the following steps:

Synthesis of the nucleoside monophosphates starting from nucleosides by enzymatic phosphorylation with a kinase according to the invention as an enzyme Use of a nucleotide triphosphate as a phosphate group donor in catalytic amounts In situ regeneration of the phosphate group donor via a regenerating system (CK/CP; PK/PEP; acetylphosphate/acylkinase, pyrophosphate/pyrophosphorylase)

As a nucleoside monophosphate according to the invention the original nucleoside monophosphates, deoxynucleoside monophosphates, dideoxynucleoside monophosphates as well as other sugar- and base-modified nucleoside monophosphates are applicable.

A further subject matter of the present invention is the use of the kinase according to the invention in the synthesis of the nucleoside monophosphate.

BRIEF DESCRIPTION OF THE FIGURES

FIG. 1:

The kinetic constants of different nucleoside kinases are listed in FIG. 1 (hTK½=human thymidine kinase ½; hdCK=human deoxy-cytidine kinase; hdGK=human deoxy-guanosine kinase; HSV=Herpes Simplex Virus). The data are taken from:

a) Munch Petersen et al. J. Biol. Chem. 266, 9032 (1991); J. Biol. Chem. 268, 15621 (1993),
b) Munch Petersen et al., Biochem. Biophys. Acta 1250, 158 (1995),
c) Bohmann and Eriksson Biochemistry, 27 4258 (1988),
d) Wang et al. J. Biol. Chemistry 268, 22847 (1993),
e) Iwatsuki et al. J. Mol. Biol. 29, 155 (1967),
f) Black et al. J. Gen. Virology 77, 1521 (1996),
g) Ma et al. P. N. A. S. 93, 14385 (1996).

FIG. 7 shows the stability of the recombinant Dm-nucleoside kinase compared to isolated Dm-nucleoside kinase. FIG. 7A was determined without addition of BSA, FIG. 7B with addition of BSA.

REFERENCES

1. Lee, L.-S. and Y.-C. Cheng (1976) Human deoxythymidine kinase. I. Purification and general properties of the cytoplasmic and mitocondrial isozymes derived from blast cells of acute myelocytic leukemia. J. Biol. Chem. 251, 2600-2604.
2. Cheng, Y.-C. and M. Ostrander (1976) Deoxythymidine kinase induced in HeLa TK cells by herpes simplex virus type I and type II. II. Purification and characterization. J. Biol. Chem., 251, 2605-2610.
3. Ellims, P. H., T. E. Gan and L. Cosgrove (1982) Human thymidine kinase: Purification and some properties of the TK1 isoenzyme from placenta, Mol. Cell. Biochem. 45, 113-116.
4. Gan, T. E., J. L. Brumley and M. B. Van Der Weyden (1983) Human thymidine kinase. Purification and properties of the cytosolic enzyme of placenta. J. Biol. Chem., 258, 7000-7004.
5. Sherley, J. L. and T. J. Kelly (1988) Human cytosolic thymidine kinase. Purification and physical characterization of the enzyme from HeLa cells, J. Biol. Chem. 263, 375-382.
6. Munch-Petersen, B., L. Cloos. G. Tyrsted and S. Eriksson (1991) Diverging substrate specificity of pure human thymidine kinases 1 and 2 against antiviral dideoxynucleosides, J. Biol. Chem., 266, 9032-9038.
7. Bohman, C. and S. Eriksson (1988) Deoxycytidine kinase from human leukemic spleen: Preparation and characterization of the homogenous enzyme. Biochemistry, 27, 4258-40265.
8. Kierdaszuk, B. and S. Eriksson (1990) Selective inactivation of the deoxyadenosine phosphorylating activity of pure human deoxycytidine kinase: Stabilization of different forms of the enzyme by substrates and biological detergents, Biochemistry, 29, 4109-4144.
9. Kristensen, T. Quantification of thymidine kinase (TK1) mRNA in normal and leukemic cells and investigation of structure-function relationship of recombinant TK1 enzyme. 1996. Department of Life Sciences and Chemistry, Roskilde University, Denmark. Ref Type: Thesis/Dissertation. Available at Roskilde University Library.
10. Hanahan D., (1983) *J Mol. Biol.* 166: 557
11. Sambrook J., Fritsch E. F., Maniatis T., (1989) *Molecular cloning: A Laboratory Manual second Edition*, B.27 Cold Spring Harbor Laboratory Press NY (USA)
12. Mullis, K. B. and Faloona, F. A., (1987) *Methods in Enzymol.* 155: 335-350
13. Munch-Peterson B., Piskur J. und Sondergaard L. (1998) *J. Biol. Chem.* 273, 3926-3931
14. Laemmli U.K. (1970) *Nature* 227: pp. 555-557

The invention is further explained by the following examples:

EXAMPLE 1

Production and Isolation of the Recombinant Dm Kinase

An *E. coli* strain BL21 was transformed with a pGEX-2T vector (Amersham Pharmacia Biotec), in which the structure gene of the Dm kinase was cloned, by means of the CaCl$_2$ method (Sam-brook, Molecular cloning, 2$^{nd}$ ed. Cold Spring Harbor Laboratory press). A transformed colony was suspended in 100 ml LB medium (10 mg tryptone, 5 mg yeast extract, 8 mg NaCl per l), containing 50 µg/ml ampicilline, over night at 37° C. The next day, the culture was adjusted to an OD of 0.6 in 1 l of LB medium and the expression was induced by 100 µl IPTG. The culture temperature of 25° C. was maintained over night and the cells were gathered by centrifugation. The cells were resuspended in 100 ml of buffer A (20 mM of potassium phosphate (pH 7.5), 5 mM MgCl$_2$, 1 mM DTT, 10% glycerin, 1% Triton X100 and 0.1 mM phenylsulfonylfluorides). The mixture was broken up by the French press. The homogenized substance was centrifuged (20000 rpm/15 min.) and filtered with a 1 µm Whatman glass micro filter and a 0.45 µm cellulose acetate filter.

The homogenized substance was applied to a GSH column (15×45 mm), equilibrated with 10 column volumes of buffer B (140 mM NaCl, 2.7 mM KCL, 10 mM Na$_2$HPO$_4$, 1.8 mM KH$_2$PO$_4$, 1 mM DTT, 10% glycerol, 1% Triton X100, 0.1, mM phenylsulfonylfluoride, 5 mM benzamidine, 50 mM aminocaproic acid). The column was washed with 50 bed volumes of buffer B and 10 volumes of buffer C (140 mM NaCl, 2.7 mM KCl, 10 mM NaH$_2$PO$_4$, 1.8 mM KH$_2$PO$_4$) and afterwards the fusion protein was split by recirculation of 1 column volume of buffer C with 400 U thrombin for 2 hours. The Dm-nucleoside kinase was then eluted with 3 column volumes of buffer C.

EXAMPLE 2

Comparison of Synthesis of d-CMP with and Without Thiol Addition

| d-Cyt | 22 mg |
| Tris buffer pH 8.0 | 2 ml |
| MgAc | 10 mg |
| ATP | 66 mg |
| d-NK | 0.132 U |
| DTT | 7 mg/0 mg |

The yield is determined by the integration of the peak areas using HPLC.

Figure 2:
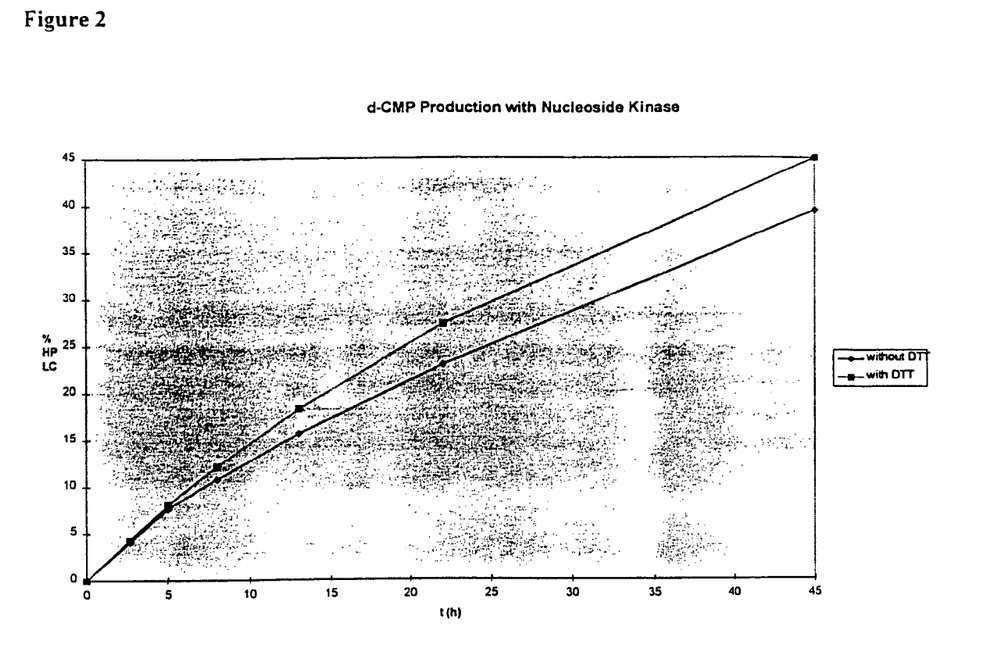
FIG. 2 shows the formation of d-CMP from cytidine under the conditions mentioned in example 2.

The reaction is not considerably slower in the preparation without DTT and is, above all, not terminated after 45 hours (see FIG. 2).

EXAMPLE 3

Synthesis of d-GMP and d-AMP

| d-Ado or d-Guo | 28 mg |
| Water | 2 ml |
| MgAc | 32 mg |
| ATP | 3 mg |
| CK | 100 U |
| d-NK | 0.396 U |
| CP (creatinphosphate) | 20 mg |

Figure 3:
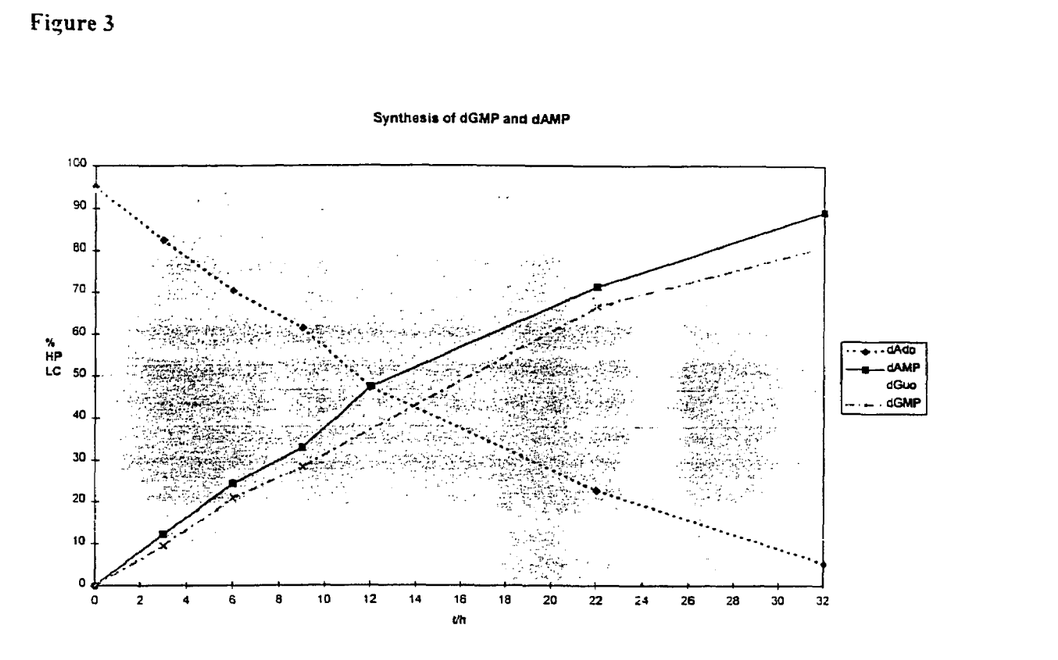
FIG. 3 shows the formation of d-AMP from adenosine and d-GMP from guanosine under the conditions mentioned in example 4.

The reaction advances for 32 hours without slowing down, the yield rate is above 80% and no thiols must be added. The addition of Tris buffer is not absolutely necessary (see FIG. 3).

EXAMPLE 4

Synthesis of d-CMP

| d-Cyt | 22 mg |
| Tris buffer pH 8.0 | 2 ml |
| MgAc | 32 mg |
| ATP | 3 mg |
| CK | 100 U |
| d-NK | 0.132 U |
| CP | 20 mg |

Figure 4:
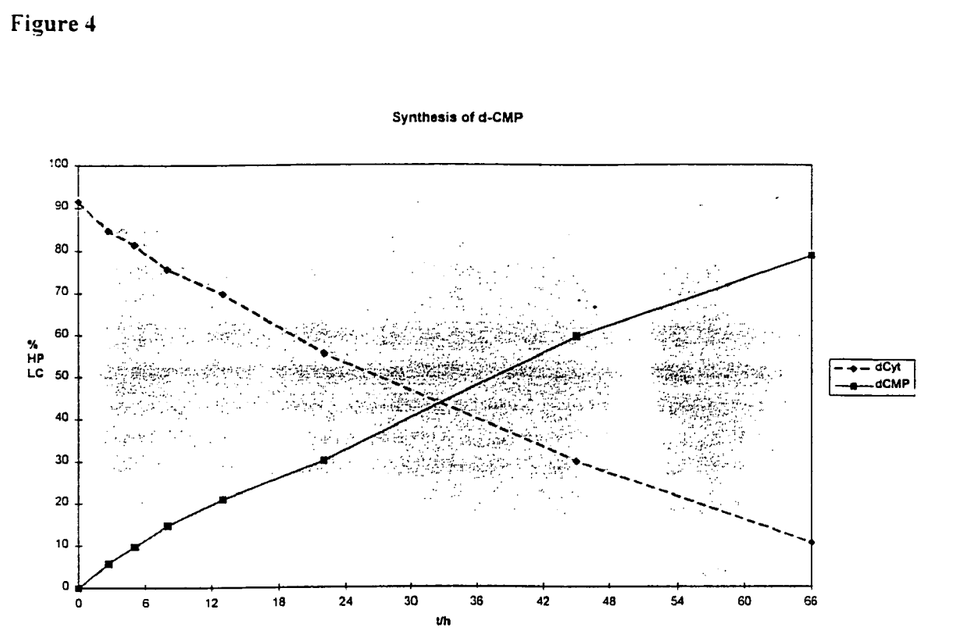
FIG. 4 shows the formation of d-CMP from cytidine under the conditions mentioned in example 3.

Even after 66 hours the enzyme is still active despite lacking thiol stabilizers. The yield rate is 80% despite the use of only catalytic ATP amounts (see FIG. 4).

EXAMPLE 5

Synthesis of NMPs, dd-NMPs and Base-Modified d-NTPs

Substrate Solution

| CP | 250 mg |
| ATP | 7 mg |
| Mg acetate | 160 mg | in 25 ml 50 mM Tris pH 8.0

An amount of each 0.5 ml of the solution is added to approx. 2.5 mg of the corresponding nucleoside. Then 50 U of the creatine kinase and 0.32 U of d-NK are added.

| Preparation | Nucleoside | Time | Yield rate |
|---|---|---|---|
| a) | Cytidine | 15 h | 90% |
| b) | dd- adenosine | 70 h | 40% |
| c) | Iso-guanosine | 2 h | 80% |

EXAMPLE 6

Activity of the kinase from *D. Melanogaster* at Different Temperatures

Figure 6:
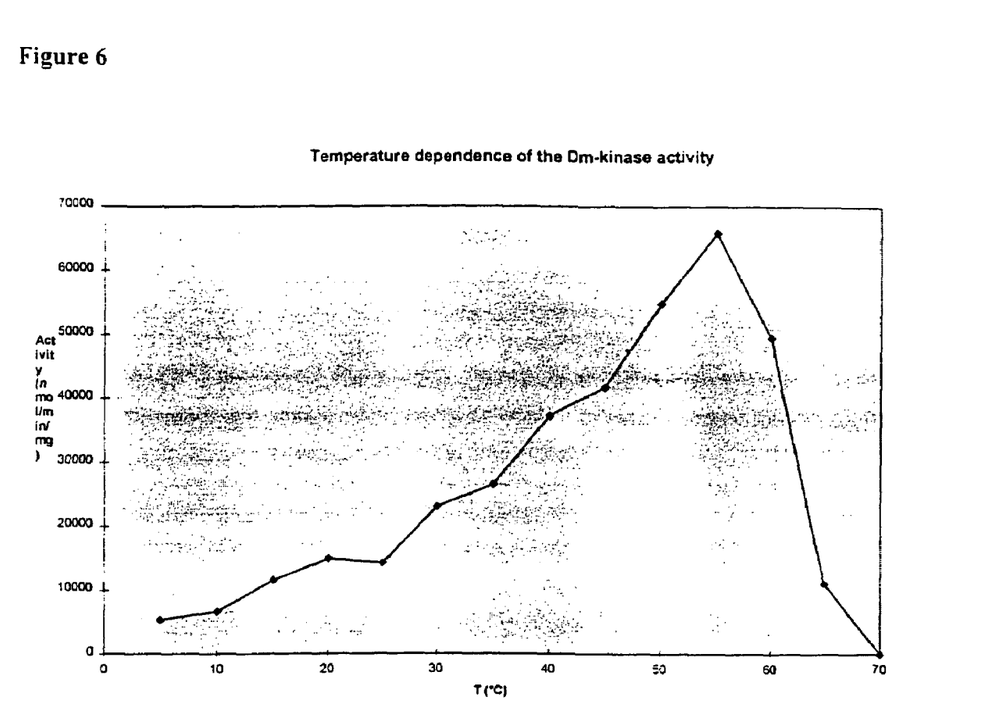
FIG. 6 shows the temperature optimum of the nucleoside kinase from *D. Melanogaster*.

The activity of the Dm-nucleoside kinase was determined at different temperatures. It shows a wide optimum with a maximum at 60° C. (see FIG. 6).

The activity test is described in reference No. 14.

EXAMPLE 7

Activity of the Recombinant Dm-Kinase Compared to Native Dm-Kinase

The activity of the recombinant Dm-kinase compared to native, isolated Dm-kinase was determined. After different periods of incubation in 50 mM Tris 7.5+2.5 mM $MgCl_2$ at 37° C. the remaining activity was determined.

Figure 7A:
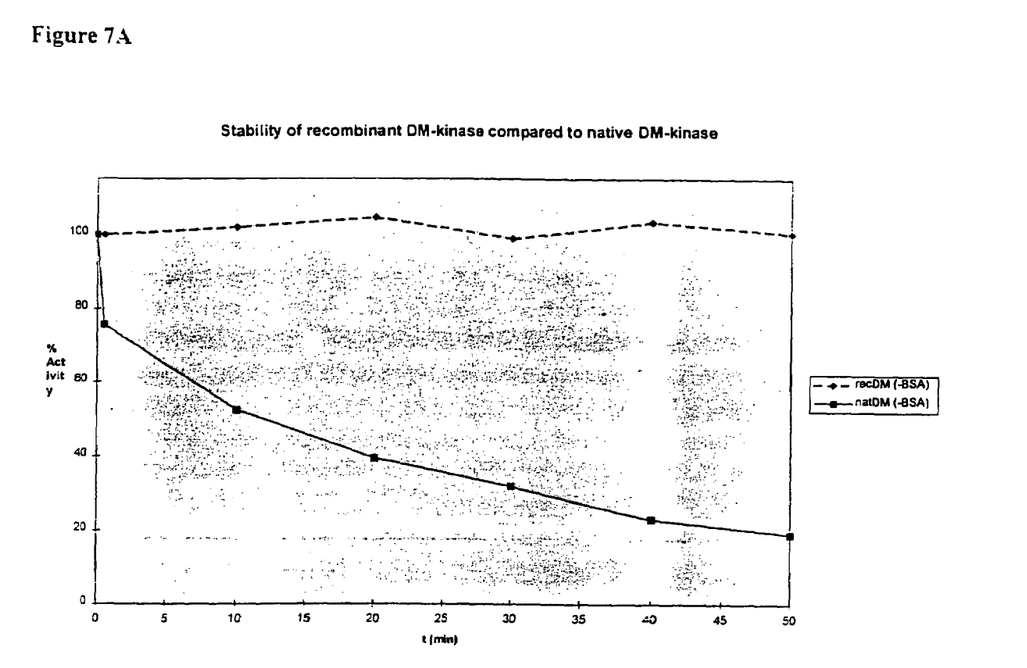
Figure 7B:
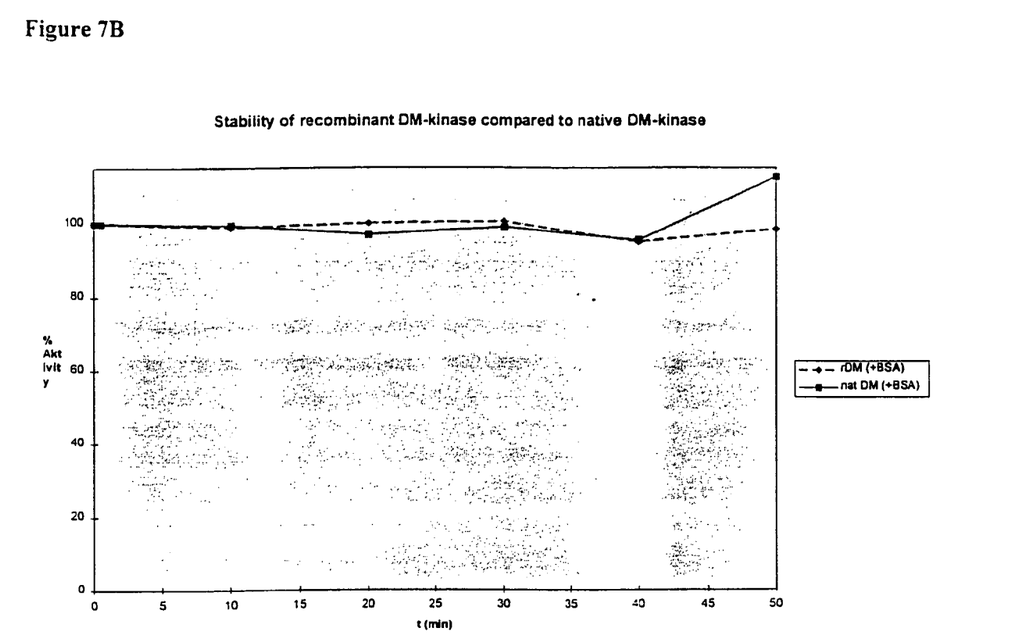

Whereas the recombinant Dm-kinase remains stable without the addition of BSA the activity of the native kinase decreases within 50 min to <20%. By adding 2.5 mg/ml BSA the native kinase remains stable as well (FIG. 7A+7B).

The half-life in Tris buffer in the presence of $MgCl_2$ is 50 h, without $MgCl_2$ 31 h and in pure water 28 h. The native Dm-kinase has a half-life of <12 min. under the same conditions.

Information for SEQ. ID. NO. 9: (DM-dNK1)
    Sequence Characteristics:
    (A) LENGTH: 21 base pairs
    (B) TYPE: nucleic acid
    (C) STRANDNESS: single
    (D) TOPOLOGY: linear

5'-TCCCAATCTCACGTGCAGATC-3'

Information for SEQ. ID. NO. 10: (DM-dNK2)
    Sequence Characteristics:
    (A) LENGTH: 21 base pairs
    (B) TYPE: nucleic acid
    (C) STRANDNESS: single
    (D) TOPOLOGY: linear

5'-TTCATCGAAGAGTCCATTCAC-3'

Information for SEQ. ID. NO. 11: (DM_dNK3)
    Sequence Characteristics:
    (A) LENGTH: 33 base pairs
    (B) TYPE: nucleic acid
    (C) STRANDNESS: single
    (D) TOPOLOGY: linear

5'-GCGCGAATTCATGGCGGAGGCAGCATCCTGTGC-3'

Information for SEQ. ID. NO. 12: (DM-dNK4)
    Sequence Characteristics:
    (A) LENGTH: 33 base pairs
    (B) TYPE: nucleic acid
    (C) STRANDNESS: single
    (D) TOPOLOGY: linear

5'-GCGCAAGCTTATTATCTGGCGACCCTCTGGC-3'

---

The invention claimed is:

1. A recombinant *Drosophila melanogaster* kinase characterized by:
- remaining stable during synthesis of nucleoside monophosphate in the absence of a stabilizing SH reagent and a stabilizing protein,
- accepting all natural deoxynucleosides, and
- being obtained by a method comprising:
- isolating a coding sequence of the recombinant *Drosophila melanogaster* kinase from *Drosophila melanogaster*, said coding sequence comprising the nucleic acid sequence of SEQ ID NO: 1;
- cloning said coding sequence into an expression vector under the control of an inducible promoter for *E. coli*,
- transforming the expression vector in an *E. coli* host strain, and
- expressing the recombinant *Drosophila melanogaster* kinase in *E. coli* cells by induction.

2. The recombinant kinase of claim 1 further characterized by having a specific activity of at least 20 U/mg (1U=1 μmol/min) for all natural deoxynucleosides.

3. The recombinant kinase of claim 1 further characterized by having a specificity constant $k_c/K_m$ of >10,000 $M^{-1}s^{-1}$ for all natural deoxynucleosides.

4. The recombinant kinase of claim 1 further characterized by having a half-life, based on measuring kinase activity, of ≧50 hours in Tris buffer with 5 mM $MgCl_2$ and of 25 hours in water at 37° C.

5. The recombinant kinase of claim 1 further characterized by having an optimum kinase activity at a temperature between 40° and 60° C.

* * * * *

UNITED STATES PATENT AND TRADEMARK OFFICE
CERTIFICATE OF CORRECTION

PATENT NO. : 7,625,735 B2
APPLICATION NO. : 10/680635
DATED : December 1, 2009
INVENTOR(S) : Ihlenfeldt et al.

It is certified that error appears in the above-identified patent and that said Letters Patent is hereby corrected as shown below:

In Claim 3, line 25, please delete "$k_c/K_m$" and insert -- $k_c/K_m$ -- in its place.

In Claim 4, line 29, please delete "25 hours" and insert -- $\geq 25$ hours -- in its place.

Signed and Sealed this

Second Day of February, 2010

David J. Kappos
*Director of the United States Patent and Trademark Office*

UNITED STATES PATENT AND TRADEMARK OFFICE
CERTIFICATE OF CORRECTION

PATENT NO. : 7,625,735 B2  Page 1 of 1
APPLICATION NO. : 10/680635
DATED : December 1, 2009
INVENTOR(S) : Ihlenfeldt et al.

It is certified that error appears in the above-identified patent and that said Letters Patent is hereby corrected as shown below:

Column 16, in Claim 3, line 25, please delete "$k_c/K_m$" and insert -- $k_c/K_m$ -- in its place.

Column 16, in Claim 4, line 29, please delete "25 hours" and insert -- $\geq 25$ hours -- in its place.

This certificate supersedes the Certificate of Correction issued February 2, 2010.

Signed and Sealed this

Twenty-third Day of February, 2010

David J. Kappos
*Director of the United States Patent and Trademark Office*

UNITED STATES PATENT AND TRADEMARK OFFICE
CERTIFICATE OF CORRECTION

PATENT NO. : 7,625,735 B2
APPLICATION NO. : 10/680635
DATED : December 1, 2009
INVENTOR(S) : Ihlenfeldt et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 627 days.

Signed and Sealed this

Second Day of November, 2010

David J. Kappos
*Director of the United States Patent and Trademark Office*

SEQUENCE LISTING

```
<160> NUMBER OF SEQ ID NOS: 14

<210> SEQ ID NO 1
<211> LENGTH: 753
<212> TYPE: DNA
<213> ORGANISM: Drosophila melanogaster

<400> SEQUENCE: 1
atggcggagg cagcatcctg tgcccgaaag gggaccaagt acgccgaggg cacccagccc      60
ttcaccgtcc tcatcgaggg caacatcggc agcgggaaga ccacgtattt gaaccacttc     120
gagaagtaca agaacgacat ttgcctgctg accgagcccg tcgagaagtg gcgcaacgtc     180
aacggggtaa atctgctgga gctgatgtac aaagatccca agaagtgggc catgcccttt     240
cagagttatg tcacgctgac catgctgcag tcgcacaccg ccccaaccaa caagaagcta     300
aaaataargg agcgctccat ttttagcgct cgctattgct tcgtggagaa catgcgacga     360
aacggctcgc tggagcaggg catgtacaat acgctggagg agtggtacaa gttcatcgaa     420
gagtccattc acctgcaggc ggacctcatc atatatctgc gcacctcgcc ggaggtggcg     480
tacgaacgca tccggcagcg ggctcgttct gaggagagct gcgtgccgct taagtacctt     540
caggagctgc atgagttgca ccaggactgg ttgatacacc agagacgacc gcagtcgtgc     600
aaggtcctag tcctcgatgc cgatctgaac ctggaaaaca ttggcaccga gtaccagcgc     660
```

```
tcggagagca gcatattcga cgccatctca agtaaccaac agccctcgcc ggttcgtgtg    720
tcgcccagca agcgccagag ggtcgccaga taa                                 753
```

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2

```
gccctcgatg aggacggtga aggg                                            24
```

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3

```
ggtcttcccg ctgccgatgt tgccctc                                         27
```

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

```
gttgcgccac ttctcgacgg gctcggtcag cag                                  33
```

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5

```
aatggagcgc tccattattt ttagctt                                         27
```

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

```
cacgaagcaa tagcgagcgc taaaaatgga                                      30
```

<210> SEQ ID NO 7
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 7
ctcctcagaa cgagcccgct gccggatgcg ttcgtacgcc ac                              42

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ccacttcttg ggatctttgt acatcag                                              27

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tcccaatctc acgtgcagat c                                                    21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ttcatcgaag agtccattca c                                                    21

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcgcgaattc atggcggagg cagcatcctg tgc                                       33

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcgcaagctt attatctggc gaccctctgg c                                         31

<210> SEQ ID NO 13
<211> LENGTH: 45
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 13
cgcgaattca tggcggaagc ggcgagctgc gcgcgtaagg ggacc              45

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cgcaagctta ttaacgggcg accctctggc                               30
```